US010258296B2

(12) United States Patent
Hiraoka et al.

(10) Patent No.: US 10,258,296 B2
(45) Date of Patent: Apr. 16, 2019

(54) X-RAY CT APPARATUS INCLUDING PROCESSING CIRCUITRY TO IMPROVE A SPATIAL RESOLUTION IN A ROW DIRECTION AND A CHANNEL DIRECTION

(71) Applicant: TOSHIBA MEDICAL SYSTEMS CORPORATION, Otawara-Shi (JP)

(72) Inventors: Manabu Hiraoka, Nasushiobara (JP); Tatsuo Maeda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 574 days.

(21) Appl. No.: 14/877,311

(22) Filed: Oct. 7, 2015

(65) Prior Publication Data

US 2016/0022237 A1    Jan. 28, 2016

Related U.S. Application Data

(63) Continuation of application No. PCT/JP2014/063714, filed on May 23, 2014.

(30) Foreign Application Priority Data

May 23, 2013   (JP) ................................ 2013-109143

(51) Int. Cl.
*A61B 6/00*   (2006.01)
*A61B 6/03*   (2006.01)
*A61B 6/06*   (2006.01)

(52) U.S. Cl.
CPC .............. *A61B 6/035* (2013.01); *A61B 6/032* (2013.01); *A61B 6/06* (2013.01); *A61B 6/4014* (2013.01);

(Continued)

(58) Field of Classification Search
CPC ........... A61B 6/032; A61B 6/035; A61B 6/06; A61B 6/4014; A61B 6/42; A61B 6/4208;
(Continued)

(56) References Cited

U.S. PATENT DOCUMENTS 6,196,715 B1 *  3/2001  Nambu .................... A61B 6/00
                                                      378/11
6,363,134 B1 *  3/2002  Suzuki ................... A61B 6/032
                                                      378/15

(Continued)

FOREIGN PATENT DOCUMENTS

JP   06-169911 A   6/1994
JP   07-084052 A   3/1995

(Continued)

OTHER PUBLICATIONS

International Preliminary Report on Patentability and Written Opinion dated Dec. 3, 2015 in PCT/JP2014/063714 filed on May 23, 2014 (English translation only).

(Continued)

*Primary Examiner* — Allen C. Ho
(74) *Attorney, Agent, or Firm* — Oblon, McClelland, Maier & Neustadt, L.L.P.

(57) ABSTRACT

An X-ray CT apparatus includes a first X-ray source, a first detector, a second X-ray source, a second detector, and processing circuitry. The processing circuitry controls the first X-ray source, the second X-ray source, the first detector, and the second detector to perform scanning. The processing circuitry acquires first data of a plurality of first detection regions and second data of a plurality of second detection regions, each of the plurality of first detection regions and the plurality of second detection regions including one detection element or a plurality of detection elements in a row direction, and the plurality of first detection regions being offset by an amount corresponding to n (0<n<1) of a (Continued)

length of each of the plurality of first detection regions in the row direction from the respective plurality of second detection regions. The processing circuitry generates image data based on the acquired first data and the acquired second data.

5 Claims, 12 Drawing Sheets

(52) U.S. Cl.
CPC .............. *A61B 6/42* (2013.01); *A61B 6/4208* (2013.01); *A61B 6/4233* (2013.01); *A61B 6/4266* (2013.01); *A61B 6/4452* (2013.01); *A61B 6/52* (2013.01); *A61B 6/5205* (2013.01); *A61B 6/5211* (2013.01)

(58) Field of Classification Search
CPC ... A61B 6/4233; A61B 6/4266; A61B 6/4452; A61B 6/52; A61B 6/5205; A61B 6/5211
USPC ............. 378/7, 9, 19, 98.8, 189; 250/370.09
See application file for complete search history.

(56) References Cited

U.S. PATENT DOCUMENTS

| | | | | |
|---|---|---|---|---|
| 6,421,412 B1 * | 7/2002 | Hsieh | A61B 6/032 378/19 |
| 6,760,399 B2 * | 7/2004 | Malamud | A61B 6/032 378/4 |
| 6,819,738 B2 * | 11/2004 | Hoffman | A61B 6/032 250/370.09 |
| 6,834,097 B2 * | 12/2004 | Yamazaki | A61B 6/488 378/19 |
| 6,876,719 B2 * | 4/2005 | Ozaki | A61B 6/032 378/4 |
| 6,922,457 B2 * | 7/2005 | Nagata | A61B 6/032 378/15 |
| 6,947,516 B2 * | 9/2005 | Okumura | A61B 6/032 378/19 |
| 6,990,175 B2 * | 1/2006 | Nakashima | A61B 6/032 378/101 |
| 7,016,455 B2 * | 3/2006 | Bruder | A61B 6/032 378/197 |
| 7,039,152 B2 * | 5/2006 | Bruder | A61B 6/032 378/62 |
| 7,085,343 B2 * | 8/2006 | Shinno | A61B 6/032 378/19 |
| 7,085,345 B2 * | 8/2006 | Nukui | A61B 6/032 378/147 |
| 7,103,138 B2 * | 9/2006 | Pelc | A61B 6/032 378/4 |
| 7,108,421 B2 * | 9/2006 | Gregerson | A61B 6/032 378/146 |
| 7,127,025 B2 * | 10/2006 | Bruder | A61B 6/032 378/8 |
| 7,130,369 B2 * | 10/2006 | Bruder | A61B 6/032 378/9 |
| 7,194,061 B2 * | 3/2007 | Fujita | A61B 6/032 378/150 |
| 7,215,733 B2 * | 5/2007 | Nabatame | A61B 6/032 378/110 |
| 7,263,157 B2 * | 8/2007 | Bruder | A61B 6/032 378/15 |
| 7,280,631 B2 * | 10/2007 | De Man | A61B 6/032 378/10 |
| 7,298,814 B2 * | 11/2007 | Popescu | A61B 6/032 378/19 |
| 7,324,623 B2 * | 1/2008 | Heuscher | A61B 6/032 378/16 |
| 7,388,940 B1 * | 6/2008 | De Man | A61B 6/032 378/4 |
| 7,397,887 B2 * | 7/2008 | Kuhn | A61B 6/032 378/19 |
| 7,403,588 B2 * | 7/2008 | Bruder | A61B 6/032 378/4 |
| 7,421,062 B2 * | 9/2008 | Okumura | A61B 6/032 378/116 |
| 7,428,292 B2 * | 9/2008 | De Man | A61B 6/032 378/4 |
| 7,433,443 B1 * | 10/2008 | Tkaczyk | A61B 6/032 378/19 |
| 7,440,536 B2 * | 10/2008 | Bruder | A61B 6/032 378/4 |
| 7,440,547 B2 * | 10/2008 | Ishiyama | A61B 6/032 378/101 |
| 7,443,945 B2 * | 10/2008 | Bruder | A61B 6/032 378/7 |
| 7,473,901 B2 * | 1/2009 | Scholz | A61B 6/032 250/363.08 |
| 7,535,987 B2 * | 5/2009 | Matsuda | G01N 23/046 378/159 |
| 7,564,937 B2 * | 7/2009 | Nakanishi | A61B 6/032 378/4 |
| 7,583,784 B2 * | 9/2009 | Andreas | A61B 6/032 378/4 |
| 7,609,803 B2 * | 10/2009 | Okamoto | A61B 6/032 378/7 |
| 7,616,730 B2 * | 11/2009 | Flohr | A61B 6/032 378/8 |
| 7,616,731 B2 * | 11/2009 | Pack | G01N 23/046 378/10 |
| 7,623,617 B2 * | 11/2009 | Popescu | A61B 6/032 378/7 |
| 7,636,415 B2 * | 12/2009 | Popescu | A61B 6/032 378/7 |
| 7,656,992 B2 * | 2/2010 | Bruder | A61B 6/032 378/8 |
| 7,706,499 B2 * | 4/2010 | Pack | A61B 6/027 378/10 |
| 7,711,081 B2 * | 5/2010 | Bruder | A61B 6/032 378/4 |
| 7,801,265 B2 * | 9/2010 | Yu | A61B 6/032 378/4 |
| 7,831,012 B2 * | 11/2010 | Foland | G01N 23/04 378/57 |
| 7,835,486 B2 * | 11/2010 | Basu | A61B 6/027 378/10 |
| 7,856,134 B2 * | 12/2010 | Rührnschopf | A61B 6/032 382/128 |
| 7,869,561 B2 * | 1/2011 | Dafni | A61B 6/032 378/19 |
| 7,876,874 B2 * | 1/2011 | Goto | A61B 6/032 378/5 |
| 7,920,671 B2 * | 4/2011 | Okumura | A61B 6/032 378/4 |
| 7,949,089 B2 * | 5/2011 | Dafni | A61B 6/022 378/6 |
| 8,189,736 B2 * | 5/2012 | Hirokawa | A61B 6/032 378/15 |
| 8,340,241 B2 * | 12/2012 | Adachi | A61B 6/032 378/15 |
| 8,483,352 B2 * | 7/2013 | Hoffman | A61B 6/032 378/19 |
| 8,488,736 B2 * | 7/2013 | Hoffman | A61B 6/032 378/19 |
| 8,509,380 B2 * | 8/2013 | Pelc | A61B 6/032 378/9 |
| 8,731,265 B2 * | 5/2014 | Nakanishi | A61B 6/032 378/4 |
| 8,774,351 B2 * | 7/2014 | Funk | A61B 6/4488 378/62 |
| 9,282,935 B2 * | 3/2016 | Tsukagoshi | A61B 6/032 |
| 9,380,987 B2 * | 7/2016 | Kojima | G01T 1/2002 |
| 9,389,320 B2 * | 7/2016 | Ogawa | A61B 6/14 |
| 9,433,388 B2 * | 9/2016 | Noshi | A61B 6/032 |
| 9,498,168 B2 * | 11/2016 | Allmendinger | A61B 6/035 |
| 9,532,759 B2 * | 1/2017 | Taguchi | A61B 6/032 |

(56) References Cited

U.S. PATENT DOCUMENTS 9,747,704 B2 * 8/2017 Taguchi ................ G06T 11/005
9,818,182 B2 * 11/2017 Ueki ..................... G06T 7/0012

FOREIGN PATENT DOCUMENTS

| JP | 2001-346791 A | 12/2001 |
| JP | 2004-000356 A | 1/2004 |
| JP | 2004-325183 A | 11/2004 |
| JP | 2006-122483 A | 5/2006 |
| JP | 2006-187453 A | 7/2006 |
| JP | 2007-044391 A | 2/2007 |
| JP | 2011-104075 A | 6/2011 |

OTHER PUBLICATIONS

International Search Report dated Jul. 15, 2014 in PCT/JP2014/063714 filed May 23, 2014, with English translation.

* cited by examiner

X-RAY CT APPARATUS INCLUDING PROCESSING CIRCUITRY TO IMPROVE A SPATIAL RESOLUTION IN A ROW DIRECTION AND A CHANNEL DIRECTION

CROSS-REFERENCE TO RELATED APPLICATION

This application is a Continuation application of No. PCT/JP2014/63714, filed on May 23, 2014, and the PCT application is based upon and claims the benefit of priority from Japanese Patent Application No. 2013-109143, filed on May 23, 2013, the entire contents of which are incorporated herein by reference.

FIELD

The present embodiment as an aspect of the present invention relates to an X-ray CT (computed tomography) apparatus for generating image data.

BACKGROUND

In X-ray CT (computed tomography), a fan-shaped X-ray beam is provided from an X-ray source to irradiate an object, and the transmitted X-rays are measured by an X-ray detector including a plurality of detection elements which are arranged in accordance with the expansion of the fan-shaped X-ray beam.

Then, the measurement of transmitted X-rays is performed in multiple view directions while the X-ray source and the detection element array are rotated around the object. Such measurement of transmitted X-rays is called "scanning". Then, based on the measured data of multiple views obtained by scanning, a tomogram of the object is reconstructed.

There are disclosed techniques for improving spatial resolution of a tomogram in a channel direction by advantageously devising the arrangement of the plurality of detection elements of one X-ray detector.

However, such prior art cannot improve the spatial resolution of a tomogram in a row direction (z-axis direction) of the detection elements.

Moreover, in the prior art, there is no technique available, in a two-tube system, to improve the spatial resolution of a tomogram in a channel direction.

BRIEF DESCRIPTION OF THE DRAWINGS

In accompanying drawings.

DETAILED DESCRIPTION

An X-ray CT apparatus of the present embodiment will be described with reference to appended drawings.

To solve the above-described problems, the present embodiment provides the X-ray CT apparatus, including a first X-ray source, a first detector, a second X-ray source, a second detector, and a processing circuitry. The first X-ray source emits a first X-ray. The first detector includes a plurality of detection elements in a channel direction and a row direction, and detects the first X-ray. The second X-ray source emits a second X-ray. The second detector includes a plurality of detection elements in a channel direction and a row direction, and detects the second X-ray. The processing circuitry controls the first and second X-ray sources and the first and second detectors to perform scanning. The processing circuitry acquires first data of a plurality of first detection regions (the first detector) and second data of a plurality of second detection regions, each of the first and second detection regions (the second detector) including one detection element or a plurality of detection elements in the row direction, and the first detection regions being shifted by an amount corresponding to n (0<n<1) of the detection regions in the row direction from the respective second detection regions. The processing circuitry generates image data based on the acquired first and second data.

First Embodiment

An X-ray CT apparatus according to a first embodiment has a configuration in which the rotational trajectories of two X-ray detectors are shifted in the row direction of the detection elements, and one detection element of each X-ray detector works as one detection (counting) region.

Figure 1:
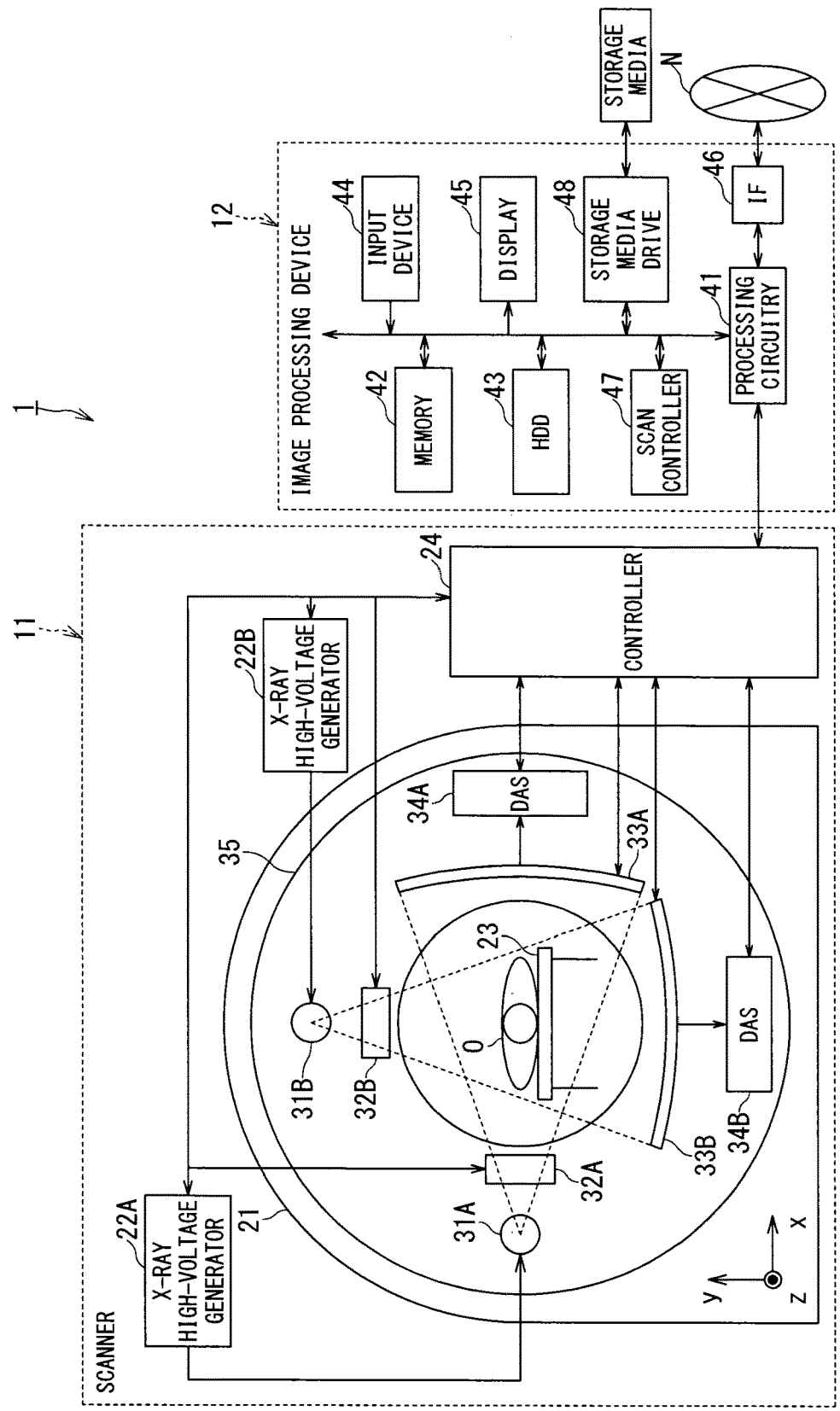
FIG. 1 is a diagram showing an exemplary configuration of an X-ray CT apparatus according to a first embodiment.
Figure 2:
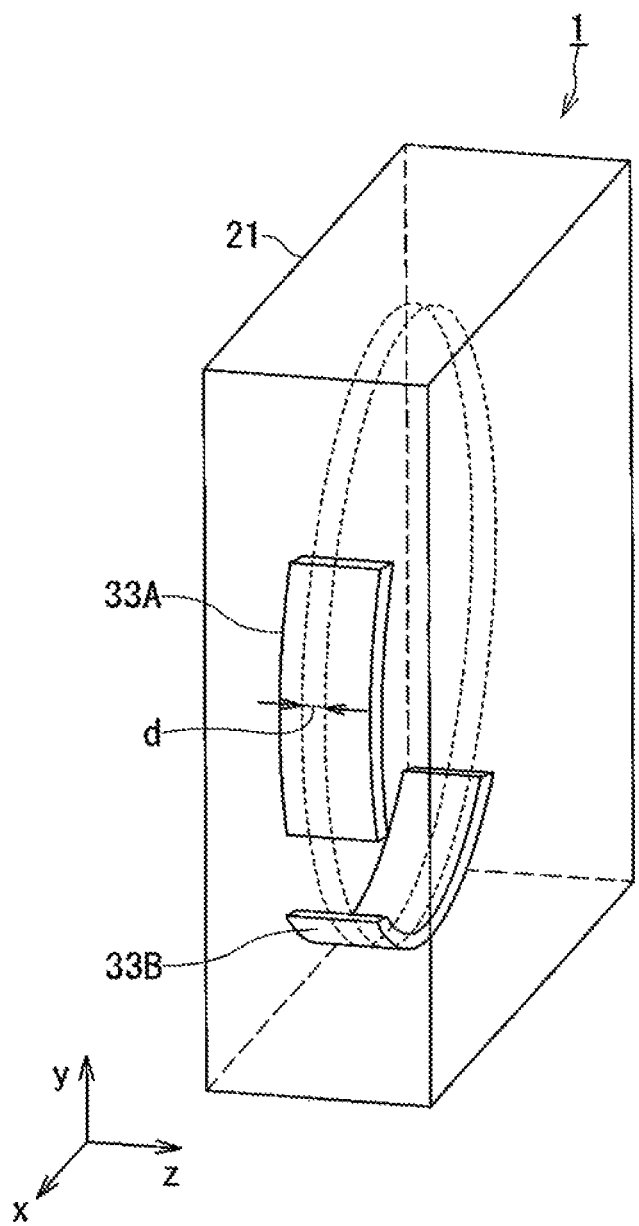
FIG. 2 is a perspective view showing a part of a configuration (gantry) of the X-ray CT apparatus according to the first embodiment.

FIG. 1 is a diagram showing an exemplary configuration of the X-ray CT apparatus according to a first embodiment. FIG. 2 is a perspective view showing a part of a configuration (gantry) of the X-ray CT apparatus according to the first embodiment.

FIGS. 1 and 2 show an X-ray CT apparatus 1 including a two-tube system according to the first embodiment. The X-ray CT apparatus 1 is generally made up of a scanner 11 and an image processing device (console) 12. The scanner 11 of the X-ray CT apparatus 1, which is usually installed in an inspection room, is configured to generate transmission data of X-rays relating to a patient O (object). On the other hand, the image processing device 12, which is usually installed in a control room adjacent to the inspection room, is configured to generate and display a tomogram based on the transmission data.

The scanner 11 of the X-ray CT apparatus 1 includes a gantry 21, X-ray high-voltage generators 22A and 22B, a bed 23, and a controller 24. Further, the gantry 21 is provided with X-ray tubes 31A and 31B, aperture mechanisms 32A and 32B, X-ray detectors 33A and 33B, DASs (data acquisition systems) 34A and 34B, and a rotating section 35. Note that the X-ray high-voltage generators 22A and 22B may be held by the gantry 21.

The X-ray tube 31A (31B) generates X-rays by causing an electron beam to collide with a target made of metal according to the tube voltage supplied from the X-ray high-voltage generator 22A (22B), and directs the X-rays toward the X-ray detector 33A (33B). A fan-beam X-ray and a cone-beam X-ray are formed by the X-rays emitted from the X-ray tube 31A (31B). The X-ray tube 31A (31B) is supplied with electric power needed for the emission of X-rays through the control by the controller 24 via the X-ray high-voltage generator 22A (22B). Although, here, the X-ray tube 31A and the X-ray tube 31B are illustrated as being shifted by 90 degrees in their views from each other, the configuration will not be limited to such a case.

The aperture mechanism 32A (32B) adjusts the emission range of X-rays to be emitted from the X-ray tube 31A (31B) in a slice direction (z-axis direction) by means of an aperture driving unit (not shown). That is, by adjusting the opening of the aperture mechanism 32A (32B) by the aperture driving unit (not shown), it is possible to change the X-ray emission range in the slice direction.

The X-ray detector 33A (33B) is a detector of a matrix-shaped, that is, of a two-dimensional array type (also called a multi-slice detector), which has a plurality of detection elements both in the channel direction and the slice direction. Moreover, the shape in the channel direction of the X-ray detector 33A (33B) is configured to be curved considering the spread angle of the X-ray beam from the X-ray tube 31A (31B). Note that the shape in the channel direction of the X-ray detector 33A (33B), which depends on its applications, may be configured not to be curved. The X-rays that have transmitted through a patient O are detected at every constant time by the X-ray detector 33A (33B), and analog values are outputted for each detection element.

The X-ray detector 33B is disposed so as to be shifted by an amount corresponding to n (0<n<1) of detection elements in the row direction with respect to the X-ray detector 33A. Hereafter, unless otherwise stated, description will be made on a case in which the X-ray detector 33B is disposed so as to be shifted by an amount corresponding to a half (½) of the detection element in the row direction with respect to the X-ray detector 33A.

Figure 3:
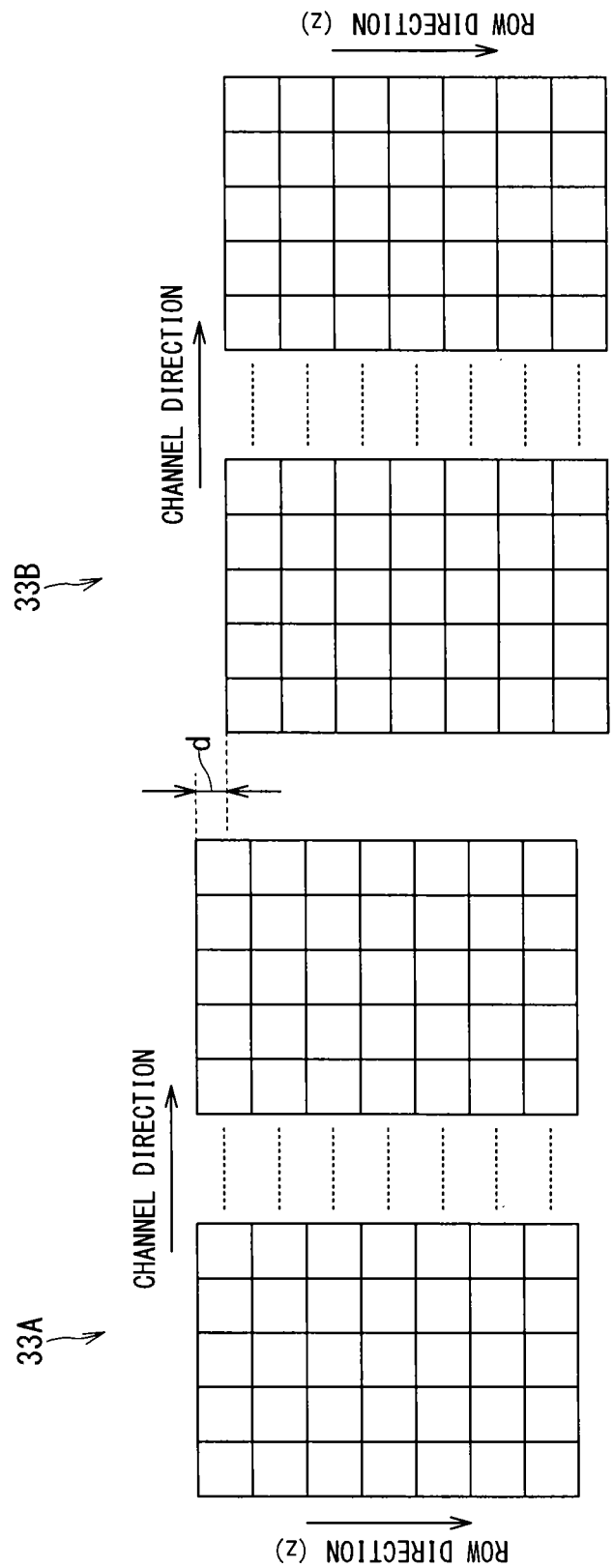
FIG. 3 is a diagram showing an exemplary configuration of the X-ray detectors.

FIG. 3 is a diagram showing an exemplary configuration of the X-ray detectors 33A and 33B.

FIG. 3 illustrates X-ray detectors 33A and 33B of a two-dimensional array type, respectively showing detection elements in multiple row/multiple channel X-ray detectors 33A and 33B in the same view. As shown in FIG. 3, the X-ray detector 33B is disposed so as to be shifted by an amount corresponding to ½ of the detection element (a length d) in the row direction with respect to the X-ray detector 33A. That is, the rotational trajectories of the X-ray detectors 33A and 33B are shifted by an amount corresponding to ½ of the detection element (a length d) in the row direction from each other (see FIG. 2).

By configuring the X-ray detectors 33A and 33B in this way, the X-ray CT apparatus 1 (shown in FIG. 1) can detect transmission data at an interval of ½ detection element, that is, at twice the resolution in the row direction in each view.

Note that in the X-ray detectors 33A and 33B shown in FIG. 3, for convenience sake, the detection elements are illustrated as being disposed in a planar manner, but they will not be limited to such a case.

Referring back to the description of FIG. 1, DAS 34A (34B) detects X-rays that are incident on a detection region (one detection element in the first embodiment) of the X-ray detector 33A (33B) with an integrator (not shown) during a constant time period until being reset. Analog values as a result of the detection are subjected to A/D conversion and read out as detection data (raw data) in digital quantities.

The rotating section 35 holds the X-ray tubes 31A and 31B, the aperture mechanisms 32A and 32B, the X-ray detectors 33A and 33B, and DASs 34A and 34B as a, single body with the X-ray tube 31A (31B) and the X-ray detector 33A (33B) being opposed to each other. The rotating section 35 is configured so as to be able to rotate the X-ray tubes 31A and 31B, the aperture mechanisms 32A and 32B, the X-ray detectors 33A and 33B, and DASs 34A and 34B as a single body around the patient O through the control by the controller 24 via a rotation drive unit (not shown). Note that the direction parallel with the rotational center axis of the rotating section 35 is defined by a z-axis direction, the plane orthogonal to the z-axis direction is defined by an x-axis direction and a y-axis direction.

The X-ray high-voltage generator 22A (22B) supplies electric power, which is needed for the emission of X-rays, to the X-ray tube 31A (31B) through the control by the controller 24.

The bed 23 can place the patient O thereon. The bed 23 is moved up and down in the y-axis direction, and is moved forward and backward along the z-axis direction through the control by the controller 24 via a bed driving unit (not shown). The central portion of the rotating section 35 has an opening, and the bed 23 on which the patient O is placed is inserted into the opening.

The controller 24 includes a processing circuitry such as a CPU (central processing unit) not shown, and a memory, etc. The controller 24 performs the control of the gantry 21, the X-ray high-voltage generators 22A and 22B, and the bed 23 etc. according to the instruction from the image processing device 12, causing the scanning to be carried out.

The image processing device 12 of the X-ray CT apparatus 1 is configured based on a computer, and is mutually communicable with a network (e.g., a local area network) N. The image processing device 12 is generally made up of basic hardware such as processing circuitry 41, a memory 42, an HOD (hard disc drive) 43, an input device 44, a display 45, an IF (interface) 46, and a scan controller 47, etc. The processing circuitry 41 is interconnected with each hardware component constituting the image processing device 12 via a bus as a common signal transmission path.

The processing circuitry 41 is processing circuitry having a configuration of an integrated circuit (LSI: Large-Scale Integration) enclosed in a package, in which electronic circuits made up of semiconductors have a plurality of terminals. Upon being input an instruction by an operator such as a radiologist operating the input device 44, the processing circuitry 41 executes a program stored in the memory 42. Alternatively, the processing circuitry 41 loads a program stored in a HDD 43, a program transferred from a network N and installed in the HDD 43, or a program read out from a storage media mounted on a storage media drive 48 and installed onto the HDD 43, on the memory 42 and executes it.

Figure 4:
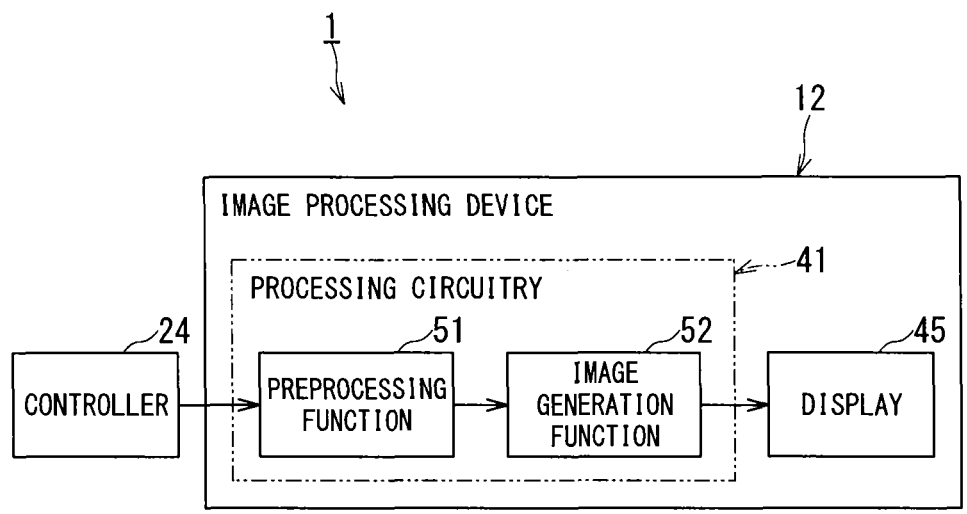
FIG. 4 is a block diagram showing functions of the X-ray CT apparatus according to the first embodiment.

The processing circuitry 41 means a special-purpose or general-purpose CPU or MPU (microprocessor unit) as well as an application specific integrated circuit (ASIC), programmable logic device, and the like. Examples of the programmable logic device include a simple programmable logic device (SPLD), a complex programmable logic device (CPLD), and a field programmable gate array (FPGA). Functions 51 and 52 shown in FIG. 4 are implemented when the processing circuitry 41 reads out and executes programs stored in memory 42 or directly incorporated in the processing circuitry 41.

Also, the processing circuitry 41 may be made up of a single circuit or a combination of plural independent circuits. In the latter case, a plurality of memories 42 may be provided for each of the plural independent circuits or a single memory 42 may store programs corresponding to functions of the plural independent circuits.

The memory 42 is a storage device including a ROM (read only memory) and a RAM (random access memory), etc. The memory 42 is used to store IPL (initial program loader), BIOS (basic input/output system), and data, and to temporarily store the work memory and data of the processing circuitry 41.

The HDD 43 is a storage device having a configuration in which a metal disc coated or vapor-deposited with a magnetic material is non-removably built in. The HDD 43 is a storage device that stores programs (including OS (operating system), etc. in addition to application programs) and data installed in the image processing device 12. Moreover, it is also possible to configure that the OS provides a GUI (graphical user interface) which frequently uses graphics for displaying information to the display 45 for an operator such as a radiologist, and allows basic operations to be performed by the input device 44.

The input device 44 is a pointing device which can be operated by an operator, and input signals according to the operation are sent to the processing circuitry 41.

The display 45 includes an image composing circuit not shown, a VRAM (video random access memory), and a display, etc. The image composing circuit generates composed data in which image data is composed with character data of various parameters, etc. The VRAM develops composed data onto the display. The display is made up of a liquid crystal display (LCD) or a CRT (cathode ray tube), etc. and displays images.

IF 46 is made up of connectors conforming to parallel connection specifications or serial connection specifications. IF 46 has a function of performing communication control according to each standard and connecting to a network N through a telephone line etc., thereby allowing the X-ray CT apparatus 1 to be connected to the network N.

The scan controller 47 has a function of controlling the controller 24 to execute conventional scanning or helical scanning, and a function of acquiring, respectively, from DASs 34A and 34B (shown in FIG. 1), first raw data (data before pre-processing) and second raw data, in which detection elements corresponding to each other in the plurality of detection elements of the X-ray detector 33A and the plurality of detection elements of the X-ray detector 33B are shifted from each other by an amount corresponding to ½ of the detection element (a length d shown in FIG. 2) in the row direction.

When executing a full scan (360 degrees) by a conventional scanning, the scan controller 47 causes the rotating section 35 to rotate by 360 degrees via the controller 24, and causes the X-ray detectors 33A and 33B respectively to detect transmission data for 360 degrees. On the other hand, when executing a half scan (180 degrees+a fan angle), the scan controller 47 causes the rotating section 35 to rotate by 180 degrees via the controller 24, and causes the X-ray detectors 33A and 33B respectively to detect transmission data for 180 degrees.

FIG. 4 is a block diagram showing functions of the X-ray CT apparatus 1 according to the first embodiment.

As a result of executing programs, the processing circuitry 41 of the image processing device 12 functions as a preprocessing function 51 and an image generation function 52 as shown in FIG. 4. Although the functions 51 and 52 will be described by taking an example in which they function in a software manner, part or all of the functions 51 and 52 may be provided in a hardware manner respectively in the image processing device 12.

The preprocessing function 51 has a function of performing logarithmic conversion processing and correction processing (preprocessing) such as sensitivity correction, etc. on the first raw data and the second raw data acquired by the scan controller 47 (shown in FIG. 1), and generating first projection data (data before reconstruction) and second projection data, respectively, to cause them to be stored in a storage device such as the HDD 43 (shown in FIG. 1). Moreover, the preprocessing function 51 has a function of performing removing processing of scattered rays on the preprocessed first and second projection data.

The image generation function 52 has a function of generating image data by an image reconstruction processing method such as an iterative method and a Fourier transform method based on the first projection data and the second projection data generated by the preprocessing function 51. The image generation function 52 has a function of causing the generated image data to be displayed on the display 45.

The image generation function 52 first collects first projection data and second projection data in the same view when conventional scanning is performed in which the aperture mechanisms 32A and 32B (shown in FIG. 1) are controlled by the scan controller 47 (shown in FIG. 1) such that X-rays are made incident on an overlapped portion in the row direction of the X-ray detectors 33A and 33B (shown in FIG. 1) in the same view. Then, the image generation function 52 calculates detected values for each part obtained by dividing one detection element into two in the row direction by applying the following Formulas (1) to (3), generates third projection data based on the first projection data and the second projection data, and generates image data based on the third projection data of the multiple views.

Figure 5:
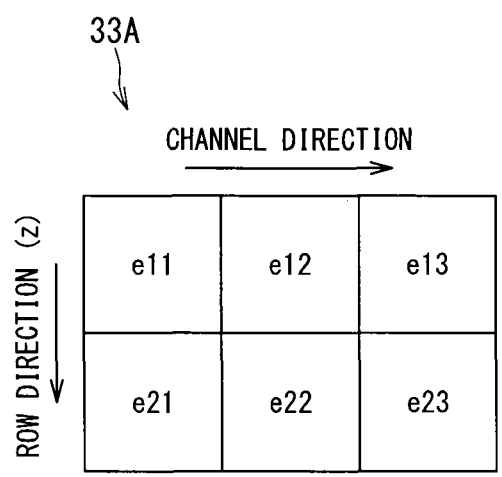
FIG. 5 is a diagram showing a spatial resolution in a row direction.
Figure 6:
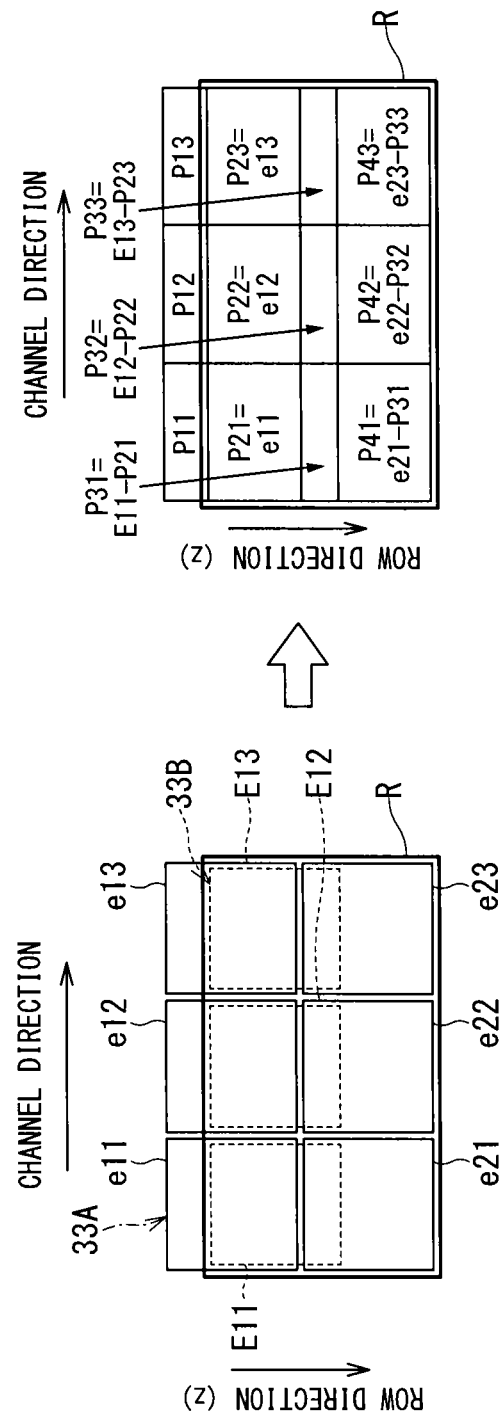
FIG. 6 is a diagram showing a spatial resolution in a row direction.
Figure 7:
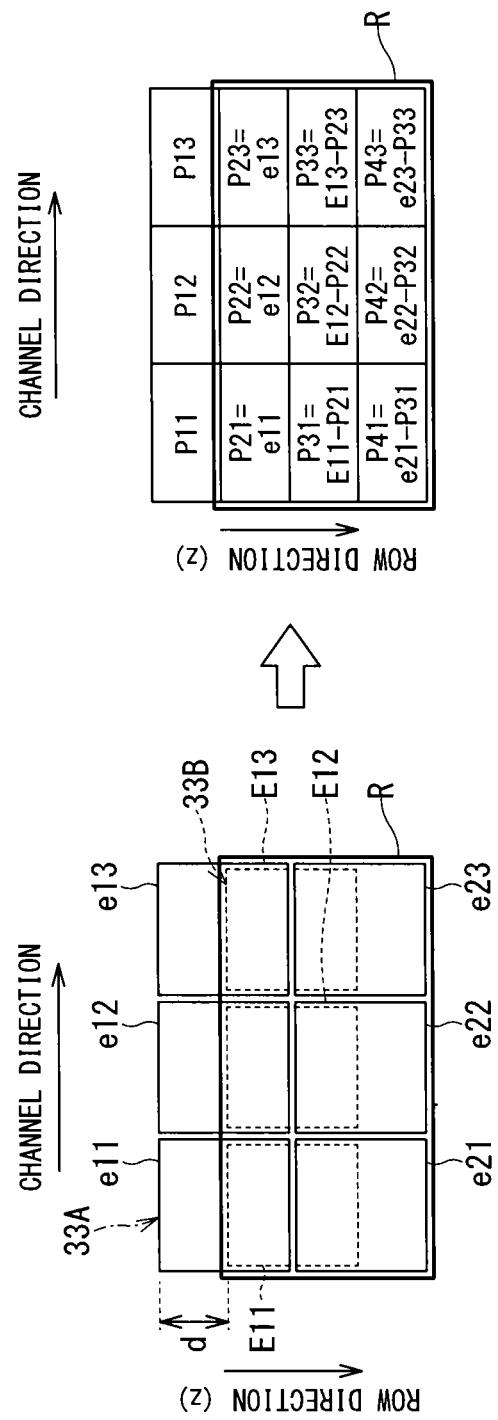
FIG. 7 is a diagram showing a spatial resolution in a row direction.

FIGS. 5, 6, and 7 are diagrams showing spatial resolution in the row direction.

FIG. 5 shows some detection elements e11 to e23 of the X-ray detector 33A. According to FIG. 5, X-rays are detected at every detection element e11 to e23, respectively.

FIGS. 6 and 7 show some detection elements e11 to e23 of the X-ray detector 33A shown in FIG. 5, and some detection elements E11 to E13 of the X-ray detector 333 when it has the same view as that of the X-ray detector 33A. In FIG. 6, the X-ray detector 33B is disposed so as to be shifted by an amount corresponding to ⅓ of the detection element in the row direction with respect to the X-ray detector 33A. On the other hand, in FIG. 7, the X-ray detector 33B is disposed so as to be shifted by an amount corresponding to ½ of the detection element (a length d) in the row direction with respect to the X-ray detector 33A.

According to FIGS. 6 and 7, it is possible to divide the detection element e11 (shown on the left-hand sides of FIGS. 6 and 7) of the X-ray detector 33A into two in the row direction to form parts P11 and P21 (shown on the right-hand sides of FIGS. 6 and 7), and is also possible to divide the detection element e21 (shown on the left-hand sides of FIGS. 6 and 7) into two in the row direction to form parts P31 and P41 (shown on the right-hand sides of FIGS. 6 and 7). Then, since the value of part P11 (shown on the right-hand sides of FIGS. 6 and 7) at the farthest end in the row direction is out of the overlapped portion R, it is possible to calculate a calculated value of part P21 from the detected value of the detection element e11 through the following Formula (1); calculate the value of part P31 from detected value of the detection element E11 and the value of part P21 through the following Formula (2); and calculate the value of part P41 from the detected value of the detection element e21 and the calculated value of part P31 through the following Formula (3).

Calculated value of part $P21$=detected value of the detection element $e11$   (1)

Calculated value of part $P31$=detected value of the detection element $E11$−calculated value of part $P21$   (2)

Calculated value of part $P41$=detected value of the detection element $e21$ calculated value of part $P31$   (3)

Note that in the case (n=⅓) shown in FIG. 6, the sizes of the parts P11 and P21 (shown on the right-hand side of FIG. 6) do not coincide with each other, but, in the case (n=½) shown in FIG. 7, the sizes of the parts P11 and P21 (shown on the right-hand side of FIG. 7) coincide with each other. Thus, whether in the case shown in FIG. 6 or in the case shown in FIG. 7, the effect of improving spatial resolution in the row direction of the detection element can be achieved.

Referring back to the description of FIG. 4, the image generation function 52, secondly, generates first volume data based on the first projection data and the second volume data based on the second projection data when conventional scanning is performed in which the aperture mechanisms 32A and 32B (shown in FIG. 1) are controlled by the scan controller 47 (shown in FIG. 1) such that X-rays are made incident on an overlapped portion in the row direction of the X-ray detectors 33A and 33B (shown in FIG. 1) in the same view. Then, the image generation function 52 calculates a detected value for each part which is obtained by dividing one detection element (voxel) into two in the row direction by applying the above described Formulas (1) to (3) based on the first volume data and the second volume data, generates third volume data, and generates the image data based on the third volume data.

When conventional scanning or helical scanning is performed by the scan controller 47 (shown in FIG. 1), the image generation function 52, thirdly, generates first image data based on the first projection data of multiple views generated by the preprocessing function 51; generates second image data based on the second projection data of multiple views generated by the preprocessing function 51; and adds up (addition averages) the first image data and the second image data to generate third image data. Moreover, in the case of conventional scanning or helical scanning, the image generation function 52 may generate first volume data based on first projection data of multiple views generated by the preprocessing function 51, and second volume data based on the second projection data of multiple views generated by the preprocessing function 51, and add up the first volume data and the second volume data to generate third volume data. In that case, image data is generated based on the third volume data.

According to the X-ray CT apparatus 1 according to the first embodiment, it is possible to improve spatial resolution in the row direction of the detection element.

Second Embodiment

An X-ray CT apparatus according to a second embodiment is configured, different from the X-ray CT apparatus according to the first embodiment, such that the rotational trajectories of two X-ray detectors coincide, and a plurality of detection elements of each X-ray detector works as one detection region.

Figure 8:
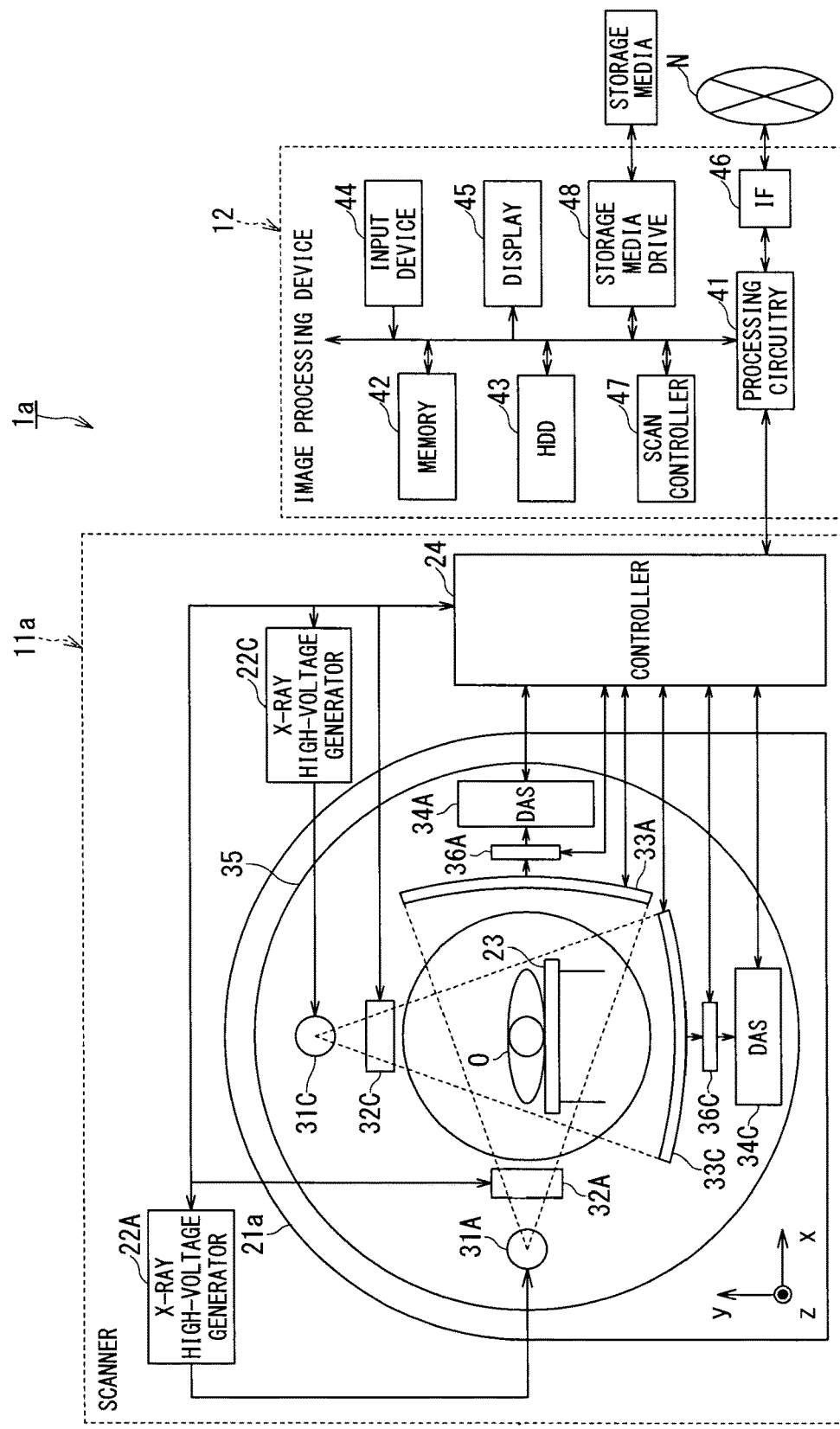
FIG. 8 is a diagram showing an exemplary configuration of an X-ray CT apparatus according to a second embodiment.
Figure 9:
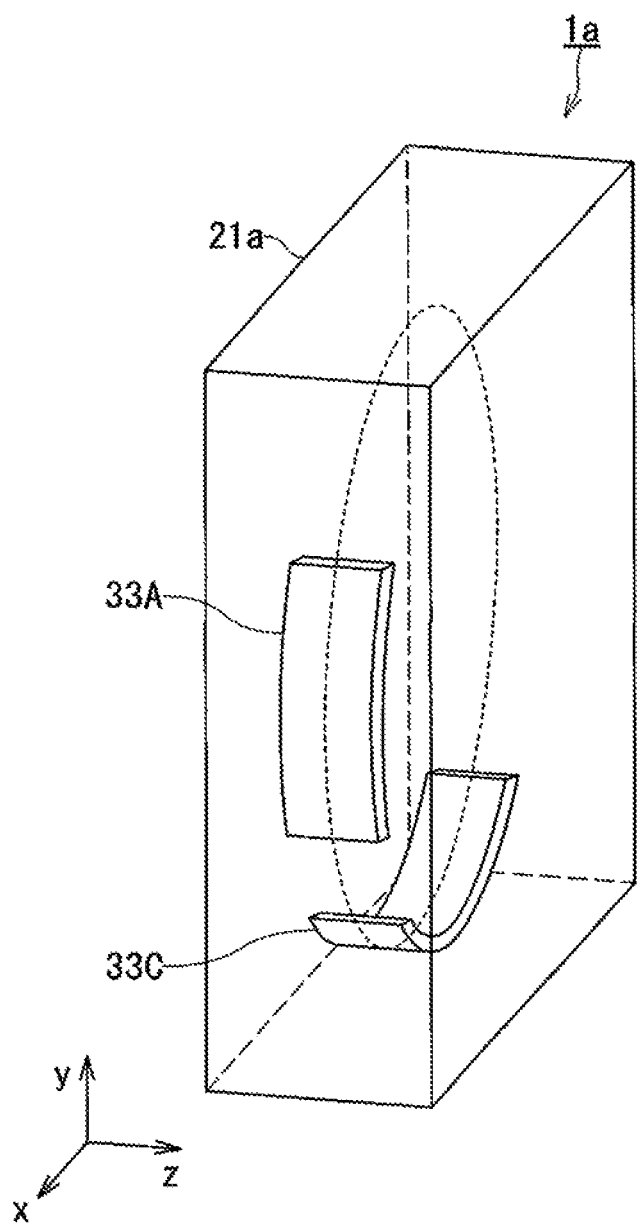
FIG. 9 is a perspective view showing a part of a configuration (gantry) of the X-ray CT apparatus according to the second embodiment.

FIG. 8 is a diagram showing an exemplary configuration of an X-ray CT apparatus according to the second embodiment. FIG. 9 is a perspective view showing a part of a configuration (gantry) of the X-ray CT apparatus according to the second embodiment.

FIGS. 8 and 9 show an X-ray CT apparatus 1a including a two-tube system according to the second embodiment. The X-ray CT apparatus 1a is generally made up of a scanner 11a and an image processing device 12. The scanner 11a of the X-ray CT apparatus 1a, which is usually installed in an inspection room, is configured to generate transmission data of X-rays relating to a patient O. On the other hand, the image processing device 12, which is usually installed in a control room adjacent to the inspection room, is configured to generate and display a tomogram based on the transmission data.

The scanner 11a of the X-ray CT apparatus 1a includes a gantry 21a, X-ray high-voltage generators 22A and 22C, a bed 23, and a controller 24. Further, the gantry 21a is provided with X-ray tubes 31A and 31C, aperture mechanisms 32A and 32C, X-ray detectors 33A and 33C, DASs 34A and 34C, a rotating section 35, and addition/switching circuits 36A and 36C. Note that the X-ray high-voltage generators 22A and 22C may be held by the gantry 21a.

Note that in the X-ray CT apparatus 1a shown in FIGS. 8 and 9, the same members as those of the X-ray CT apparatus 1 shown in FIGS. 1 and 2 are given the same reference symbols, thereby omitting description thereof.

The X-ray tube 31C generates X-rays by causing an electron beam to collide with a target made of metal according to the tube voltage supplied from the X-ray high-voltage generator 22C, and directs the X-rays toward the X-ray detector 33C. A fan-beam X-ray and a cone-beam X-ray are formed by the X-rays emitted from the X-ray tube 31C. The X-ray tube 31C is supplied with electric power needed for the emission of X-rays through the control by the controller 24 via the X-ray high-voltage generator 22C. Although, here, the X-ray tube 31A and the X-ray tube 31C are illustrated as being shifted by 90 degrees in their views from each other, the configuration will not be limited to such a case.

The aperture mechanism 32C adjusts the emission range of X-rays to be emitted from the X-ray tube 31C in a slice direction (z-axis direction) by means of an aperture driving unit (not shown). That is, by adjusting the opening of the aperture mechanism 32C by the aperture driving unit (not shown), it is possible to change the X-ray emission range in the slice direction.

The X-ray detector 33C is a detector of a matrix shape, that is, of a two-dimensional array type which has a plurality of detection elements both in the channel direction and the slice direction. Moreover, the shape in the channel direction of the X-ray detector 33C is configured to be curved considering the spread angle of the X-ray beam from the X-ray tube 31C. Note that the shape in the channel direction of the X-ray detector 33C depends on applications, and may be configured not to be curved.

DAS 34C detects X-rays that are incident on each detection region of the X-ray detector 33C by an integrator (not shown) during a constant time period until being reset. Analog values as a result of the detection are subjected to A/D conversion and read out as detection data (raw data) in digital quantity.

The addition/switching circuit 36A (36C) is disposed between the X-ray detector 33A (33C) and DAS 34A (34C).

Figure 10:
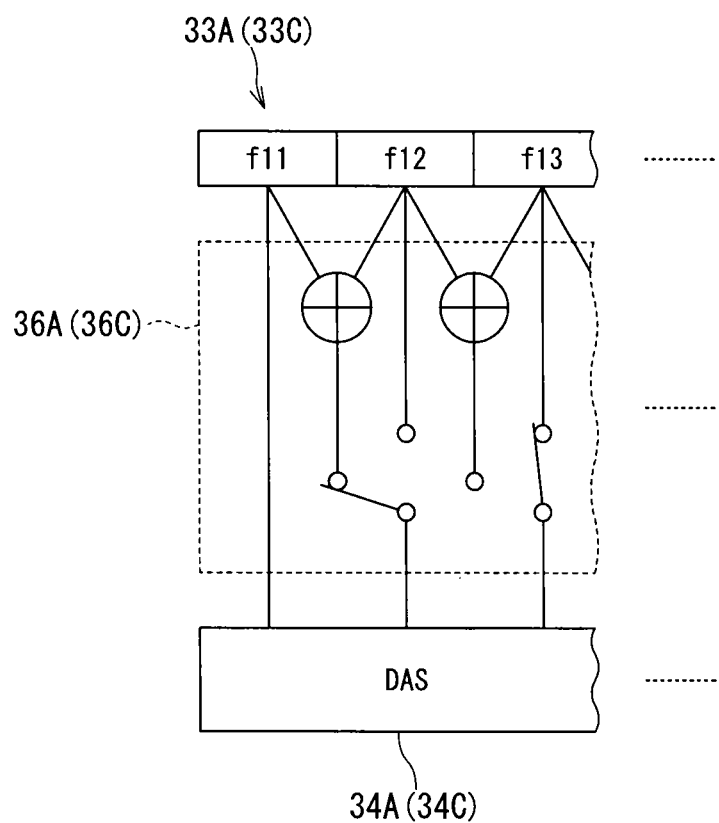
FIG. 10 is a side view showing a configuration of an addition/switching circuit.

FIG. 10 is a side view showing the configuration of the addition/switching circuit 36A (36C).

As shown in FIG. 10, the addition/switching circuit 36A (36C) is provided between subdivided detection elements of the X-ray detector 33A (33C) and DAS 34A (34C). Through the control of the controller 24 (shown in FIG. 8) via the addition/switching circuit 36A (36C), detected signals of the detection element f11 of the X-ray detector 33A (33C) may be inputted into DAS 34A (34C) as they are (detection range: one detection element), and may be added to the detected signals of the neighboring detection element f12 to be inputted into DAS 34A (34C) (detection range: two detection elements). Moreover, through the control of the controller 24 (shown in FIG. 8) via the addition/switching circuit 36A (36C), detected signals of the detection element f12 of the X-ray detector 33A (33C) may be inputted as they are into DAS 34A (34C) (detection range: one detection element); may be added to the detected signals of the neighboring detection element f11 to be inputted into DAS 34A (34C) (detection range: two detection elements); and may be added to the detected signals of the neighboring detection element f13 to be inputted into DAS 34A (34C) (detection range: two detection elements).

Figure 11:
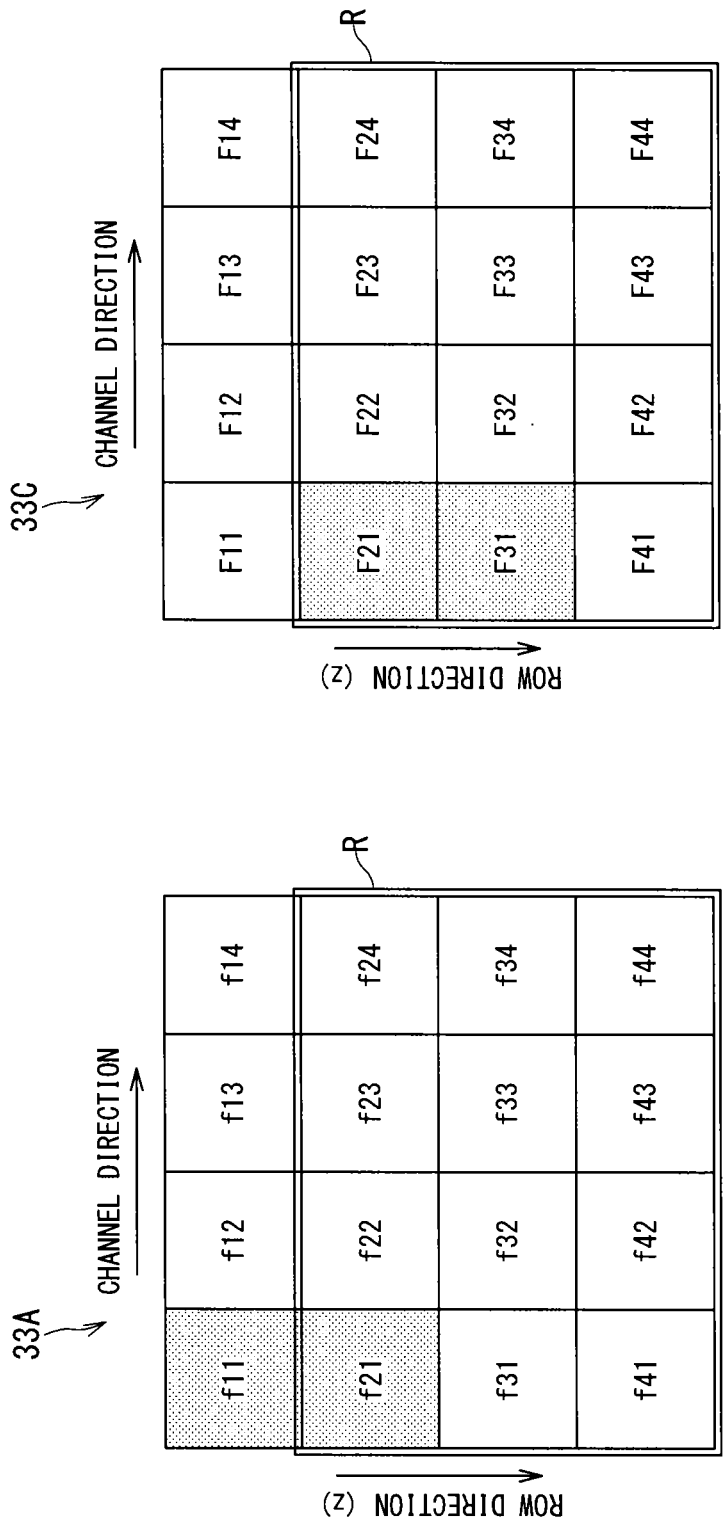
FIG. 11 is a diagram showing a method of improving spatial resolution in a row direction in the X-ray CT apparatus according to the second embodiment.

FIG. 11 is a diagram showing a method of improving spatial resolution in the row direction in the X-ray CT apparatus 1a according to the second embodiment.

FIG. 11 shows some detection elements f11 to f44 of the X-ray detector 33A, and some detection elements F11 to F44 of the X-ray detector 33C when it has the same view as that of the X-ray detector 33A.

As shown via the addition/switching circuits 36A and 36C (shown in FIGS. 8 and 10) in FIG. 11, adding detected signals of the detection elements f11 and f21 (the detection element f11 is "0" since it is out of the overlapped portion R) with the two detection elements f11 and f21 of the X-ray detector 33A being as the detection region makes it possible to generate first raw data by regarding the detection elements f11 and f21 as one detection element e11 (shown in FIG. 7); and adding detected signals of the detection elements F21 and F31 with two detection elements F21 and F31 of the X-ray detector 33C being as the detection region makes it possible to generate second raw data by regarding the detection elements F21 and F31 as one detection element E11 (shown in FIG. 7). That is, in the X-ray CT apparatus 1a according to the second embodiment, in spite of that the rotation trajectories of the two X-ray detectors 33A and 33C coincide, it is possible to increase the spatial resolution in the row direction up to twice as high as the detection region considering in the same way as in the X-ray CT apparatus 1 according to the first embodiment in which the rotation trajectories of the two X-ray detectors are shifted.

Here, detection regions respectively corresponding to each other in a plurality of detection regions including a plurality of detection elements in the channel direction of the X-ray detector 33A, and a plurality of detection regions including a plurality of detection elements in the channel direction of the X-ray detector 33C, may be shifted in the channel direction by an amount corresponding to ½ of one detection region.

Figure 12:
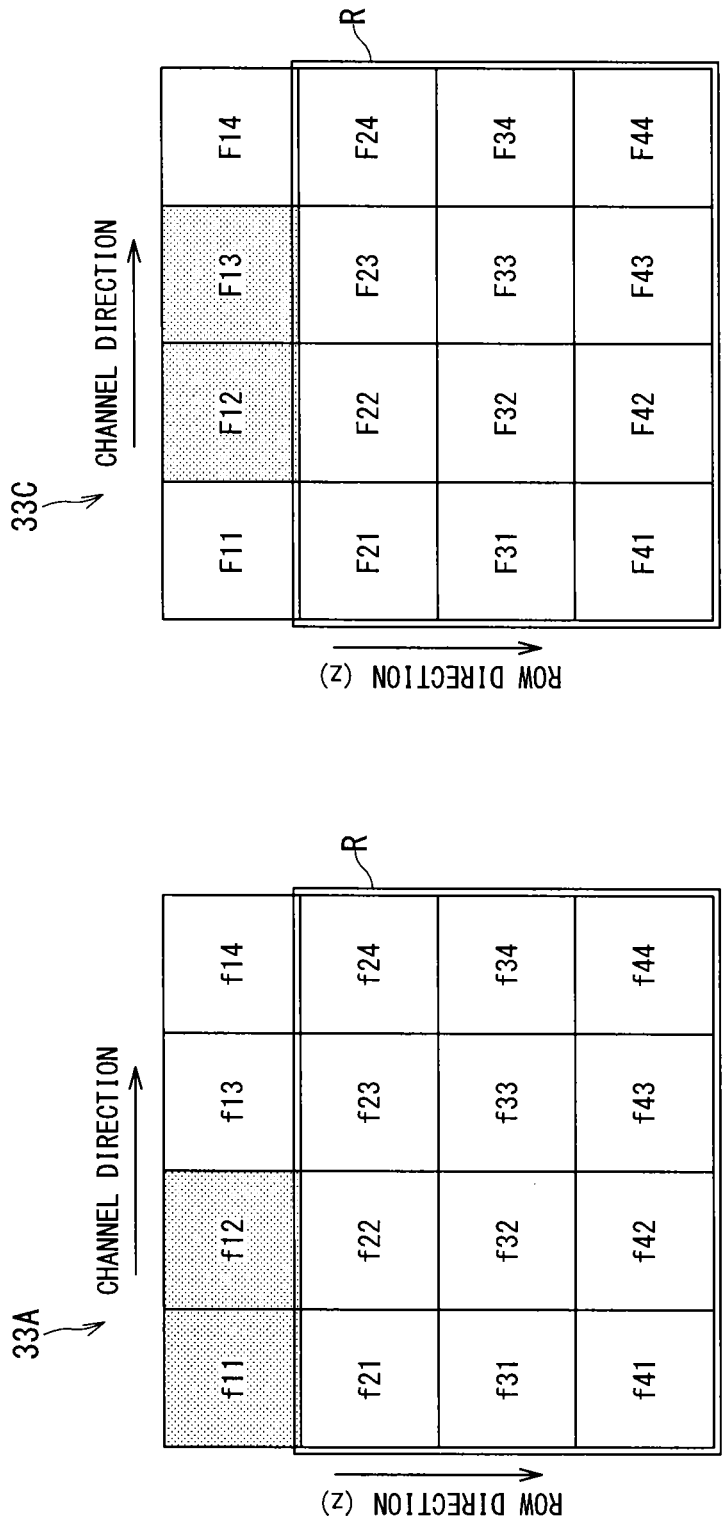
FIG. 12 is a diagram showing a method of improving spatial resolution in a channel direction in the X-ray CT apparatus according to the second embodiment.

FIG. 12 is a diagram showing a method of improving spatial resolution in the channel direction in the X-ray CT apparatus 1a according to the second embodiment.

FIG. 12 shows some detection elements f11 to f44 of the X-ray detector 33A, and some detection elements F11 to F44 of the X-ray detector 33C when it has the same view as that of the X-ray detector 33A.

As shown via the addition/switching circuits 36A and 36C (shown in FIGS. 8 and 10) in FIG. 12, adding detected signals of the detection elements f11 and f12 (the detection element f11 is "0" since it is out of the overlapped portion R) with the two detection elements f11 and f12 of the X-ray detector 33A being as the detection region makes it possible to generate first raw data by regarding the detection elements f11 and f12 as one detection element; and adding detected signals of the detection elements F12 and F13 with two detection elements F12 and F13 of the X-ray detector 33C being as the detection region makes it possible to generate second raw data by regarding the detection elements F12 and F13 as one detection element. That is, in the X-ray CT apparatus 1a according to the second embodiment, in spite of that the rotation trajectories of the two X-ray detectors 33A and 33C coincide, it is also possible to improve the spatial resolution in the channel direction to a level corresponding to twice the detection region considering in the same way as in the X-ray CT apparatus 1 according to the first embodiment in which the rotation trajectories of the two X-ray detectors are shifted.

Note that although, in FIGS. 11 and 12, description has been such that X-rays are detected at every two detection elements with two detection elements being as one detection region, detection of X-rays will not be limited to such a case.

Referring back to the description of FIGS. 8 and 9, the rotating section 35 holds the X-ray tubes 31A and 31C, the aperture mechanisms 32A and 32C, the X-ray detectors 33A and 33C, DASs 34A and 34C, and the addition/switching circuits 36A and 36C as a single body with the X-ray tube 31A (31C) and the X-ray detector 33A (33C) being opposed to each other. The rotating section 35 is configured so as to be able to rotate the X-ray tubes 31A and 31C, the aperture mechanisms 32A and 32C, the X-ray detectors 33A and 33C, DASs 34A and 34C, and the addition/switching circuits 36A and 36C as a single body around the patient O through the control by the controller 24 via a rotation drive unit (not shown). Note that the direction parallel with the rotational center axis of the rotating section 35 is defined by a z-axis direction, and a plane orthogonal to the z-axis direction is defined by an x-axis direction and a y-axis direction.

The X-ray high-voltage generator 22C supplies electric power needed for emission of X-rays to the X-ray tube 31C through the control by the controller 24.

Figure 13:
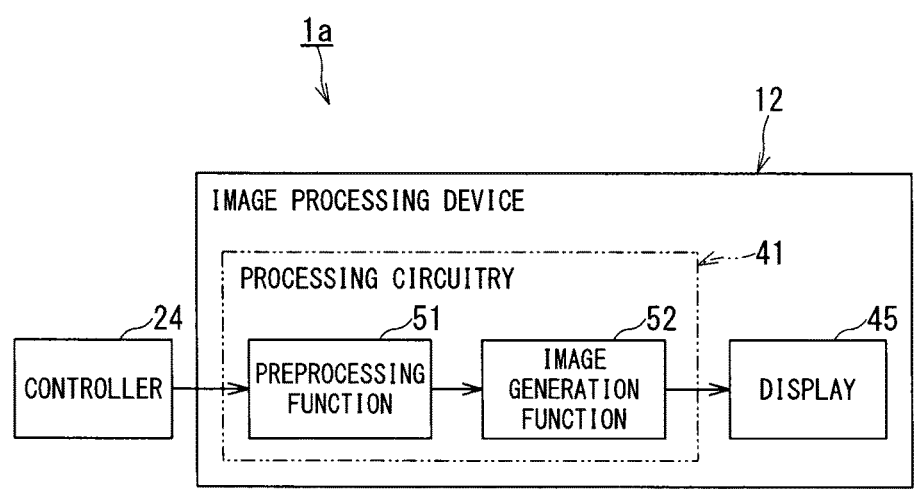
FIG. 13 is a block diagram showing functions of the X-ray CT apparatus according to the second embodiment.

FIG. 13 is a block diagram showing functions of the X-ray CT apparatus 1a according to the second embodiment.

As a result of executing programs, the processing circuitry 41 of the image processing device 12 has a preprocessing function 51 and an image generation function 52 as shown in FIG. 11. Note that in the X-ray CT apparatus 1a according to the second embodiment shown in FIG. 13, the same members as those of the X-ray CT apparatus 1 according to the first embodiment shown in FIG. 4 are given the same reference symbols, thereby omitting description thereof.

According to the X-ray CT apparatus 1a according to the second embodiment, it is possible to improve spatial resolution in the row direction of the detector. Moreover, according to the X-ray CT apparatus 1a according to the second embodiment, it is also possible to improve the spatial resolution in the channel direction of the detector even in a two-tube system.

Note that the X-ray CT apparatuses 1 and 1a of the present embodiment may be an X-ray CT apparatus of a photon-counting type. In that case, the X-ray detectors 33A to 33C detects X-rays transmitted through the patient O as X-ray photons (particles) at every constant time, and outputs analog values corresponding to photon energy for each detection element (pixel). Then, DASs 34A to 34C count the number of X-ray particles that entered into a detection region (one pixel in the first embodiment) of the X-ray detectors 33A to 33C with a plurality of counters (not shown) for each energy region corresponding to the number of stages of the counter during a constant time period until being reset. The counter values as a result of that are read out as detection data (raw data) in digital quantities from a plurality of counters. Reading of data is performed for every pixel in an ASIC layer. Moreover, although in the present embodiment, description has been made on a case in which the X-ray CT apparatus 1, 1a is a two-tube system, the X-ray CT apparatus may be a multiple-tube system such as a three-tube system.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
    a first X-ray source configured to emit a first X-ray;
    a first detector including first detection elements in a channel direction and a row direction, and configured to detect the first X-ray;
    a second X-ray source configured to emit a second X-ray;
    a second detector including second detection elements in a channel direction and a row direction, and configured to detect the second X-ray; and
    processing circuitry configured to:
        control the first X-ray source, the second X-ray source, the first detector, and the second detector to perform scanning;
        acquire first data of the first detection elements and second data of the second detection elements, wherein the first detection elements are offset by an amount corresponding to n ($0<n<1$) of a length of each first detection element in the row direction from the respective second detection elements;
        calculate data for each divided element, which is obtained by dividing each detection element in the row direction according to n, the calculated data being based on the first data and the second data acquired in a same view; and
        generate image data based on the acquired first and second data for each divided element.

2. The X-ray CT apparatus according to claim 1, further comprising:
    a first aperture mechanism and 4 second aperture mechanism configured to respectively control the first X-ray and the second X-ray so as to be incident on an overlapped portion in the row direction of the first detector and the second detector in the same view.

3. The X-ray CT apparatus according to claim 1, wherein the processing circuitry is further configured to:
    perform conventional scanning or helical scanning as the scanning;
    generate first image data based on the first data acquired in the same view by the scanning;
    generate second image data based on the second data; and
    add up the first image data and the second image data to generate third image data.

4. The X-ray CT apparatus according to claim 1, wherein a rotational trajectory of the second detector is disposed so as to coincide with a rotational trajectory of the first detector.

5. The X-ray CT apparatus according to claim 1, wherein the processing circuitry is further configured to acquire the first data and the second data, the first detection elements being offset by an amount corresponding to ½ of the length of each first detection element in the row direction from the respective second detection elements, and calculate the data for each divided element, which is obtained by dividing each detection element into two in the row direction, based on the first data and the second data acquired in the same view.

* * * * *